(12) United States Patent
Medvedev

(10) Patent No.: US 11,353,395 B2
(45) Date of Patent: Jun. 7, 2022

(54) SYSTEM AND METHOD FOR OZONE CONCENTRATION MEASUREMENT IN LIQUIDS HAVING A NEGATIVE SCALING INDEX

(71) Applicant: OWS AGRI LIMITED, London (GB)

(72) Inventor: Dmitry Medvedev, Fort Worth, TX (US)

(73) Assignee: OWS AGRI LIMITED, London (GB)

( * ) Notice: Subject to any disclaimer, the term of this patent is extended or adjusted under 35 U.S.C. 154(b) by 0 days.

(21) Appl. No.: 16/767,320

(22) PCT Filed: Jan. 23, 2018

(86) PCT No.: PCT/US2018/014768
§ 371 (c)(1),
(2) Date: May 27, 2020

(87) PCT Pub. No.: WO2019/147215
PCT Pub. Date: Aug. 1, 2019

(65) Prior Publication Data
US 2021/0003501 A1    Jan. 7, 2021

(51) Int. Cl.
*G01J 1/42* (2006.01)
*G01N 21/33* (2006.01)
*C01B 13/10* (2006.01)
*G01N 21/03* (2006.01)

(52) U.S. Cl.
CPC ............ *G01N 21/33* (2013.01); *C01B 13/10* (2013.01); *G01N 21/03* (2013.01)

(58) Field of Classification Search
CPC ........ G01N 21/33; G01N 21/03; G01N 33/00; G01N 21/31; C01B 13/10; B01J 19/12
See application file for complete search history.

(56) References Cited

U.S. PATENT DOCUMENTS 3,700,468 A    10/1972    Shore et al.
4,507,253 A     3/1985    Wiesmann
4,549,477 A    10/1985    McCabe
(Continued)

FOREIGN PATENT DOCUMENTS

DE        4342624 C1      6/1995
KR    20010055638 A   *  7/2001

OTHER PUBLICATIONS

International Search Report and Written Opinion for the International Patent Application No. PCT/US18/14768, dated Apr. 5, 2018, 8 pages.
(Continued)

*Primary Examiner* — Kiho Kim
(74) *Attorney, Agent, or Firm* — KDB Firm PLLC

(57) ABSTRACT

An apparatus includes an emitter, the emitter comprising an ultraviolet light emitting diode (UV-LED) and being disposed on a first end of a bounded volume suitable for holding a liquid. The liquid may have a negative Langelier saturation index (LSI). The bounded volume can be a chamber, a tank, or the like. The apparatus includes a detector, the detector comprising an ultraviolet light sensor (UV sensor) and being disposed on a second end of the bounded volume, the second end being opposite the first end, wherein the UV-LED comprises a point source, and wherein the emitter generates a parallel beam of light.

18 Claims, 8 Drawing Sheets

(56) References Cited

U.S. PATENT DOCUMENTS

| | | | |
|---|---|---|---|
| 4,732,480 A * | 3/1988 | Fortunato | G01N 21/31 356/453 |
| 5,334,355 A | 8/1994 | Faddis | |
| 5,420,432 A * | 5/1995 | Manook | G01N 1/14 250/373 |
| 5,632,333 A | 5/1997 | Imamura et al. | |
| 5,868,999 A | 2/1999 | Karlson | |
| 6,171,625 B1 | 1/2001 | Denvir et al. | |
| 6,485,769 B2 | 11/2002 | Audy et al. | |
| 6,518,574 B1 | 2/2003 | Castleman | |
| 6,673,248 B2 | 1/2004 | Chowdhury | |
| 6,764,659 B2 | 7/2004 | Perlov et al. | |
| 7,375,348 B1 | 5/2008 | Sickenberger et al. | |
| 8,298,418 B2 | 10/2012 | Liechti et al. | |
| 2001/0042843 A1 | 11/2001 | Cox et al. | |
| 2003/0030011 A1 | 2/2003 | Brown et al. | |
| 2004/0052702 A1 | 3/2004 | Shuman et al. | |
| 2004/0097021 A1 * | 5/2004 | Augusto | H01L 27/14632 438/149 |
| 2004/0241868 A1 | 12/2004 | Cox et al. | |
| 2005/0103723 A1 | 5/2005 | Wilkins et al. | |
| 2005/0160791 A1 | 7/2005 | Kung | |
| 2006/0240558 A1 | 10/2006 | Zhao | |
| 2008/0116054 A1 | 5/2008 | Leach et al. | |
| 2008/0304048 A1 | 12/2008 | Tormod | |
| 2009/0120473 A1 | 5/2009 | Lynn | |
| 2009/0302230 A1 * | 12/2009 | Birks | G01N 33/0039 250/373 |
| 2010/0027016 A1 * | 2/2010 | Birks | G01N 21/33 356/437 |
| 2010/0061885 A1 | 3/2010 | Harley | |
| 2010/0159601 A1 | 6/2010 | Patton | |
| 2010/0212406 A1 | 8/2010 | Browne et al. | |
| 2011/0147580 A1 | 6/2011 | Bell et al. | |
| 2011/0164245 A1 | 7/2011 | Eikelmann et al. | |
| 2012/0006098 A1 * | 1/2012 | Degner | G01N 21/3504 73/31.05 |
| 2012/0135396 A1 | 5/2012 | McDevitt et al. | |
| 2013/0045496 A1 | 2/2013 | Jansen | |
| 2013/0270429 A1 | 10/2013 | Bilenko et al. | |
| 2013/0292581 A1 | 11/2013 | Russell et al. | |
| 2014/0034840 A1 | 2/2014 | Davenport et al. | |
| 2014/0106463 A1 | 4/2014 | Wald et al. | |
| 2015/0070889 A1 | 3/2015 | Sooferian | |
| 2015/0362426 A1 * | 12/2015 | Nishino | G01N 21/3554 356/437 |
| 2016/0103089 A1 * | 4/2016 | Boyette | G01N 27/27 137/3 |
| 2016/0187214 A1 | 6/2016 | Al-Hemyari | |
| 2017/0115272 A1 | 4/2017 | Rihani et al. | |
| 2017/0219479 A1 * | 8/2017 | Bilenko | G01N 21/59 |
| 2019/0056317 A1 | 2/2019 | Clausen et al. | |

OTHER PUBLICATIONS

International Search Report and Written Opinion for the International Patent Application No. PCT/US18/13797, dated May 10, 2018, 7 pages.

International Search Report and Written Opinion for the International Patent Application No. PCT/US18/015019, dated Apr. 6, 2018, 10 pages.

Nikoleav et al., "Atmospheric Ozone Concentration Measurement by UV Light-Emitting Diode Radiation Absorption" Bulletin of the Lebedev Physics Insitute. 2013, vol. 40 (2), pp. 50-53.

International Search Report and Written Opinion for the International Patent Application No. PCT/US18/14841, dated Mar. 29, 2018, 8 pages.

International Search Report and Written Opinion for the International Patent Application No. PCT/US18/15846, dated Mar. 29, 2018, 9 pages.

International Search Report and Written Opinion for the International Patent Application No. PCT/US18/17601, dated May 7, 2018, 7 pages.

* cited by examiner

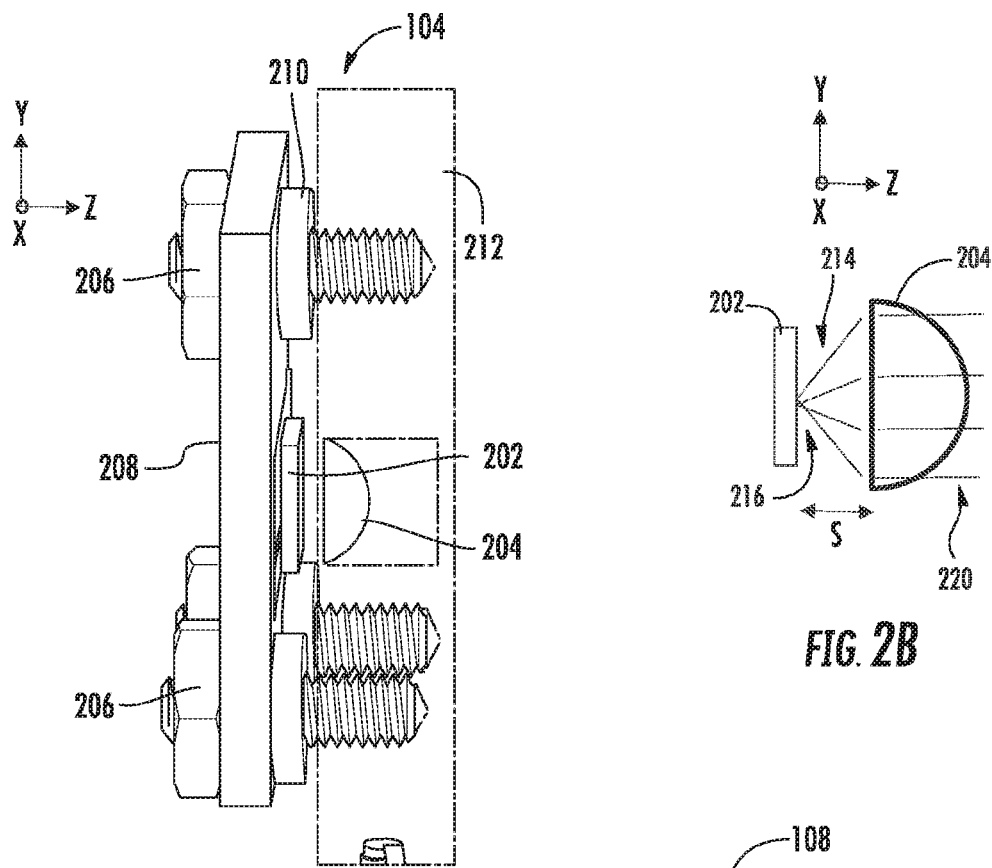
FIG. 2A
FIG. 2B
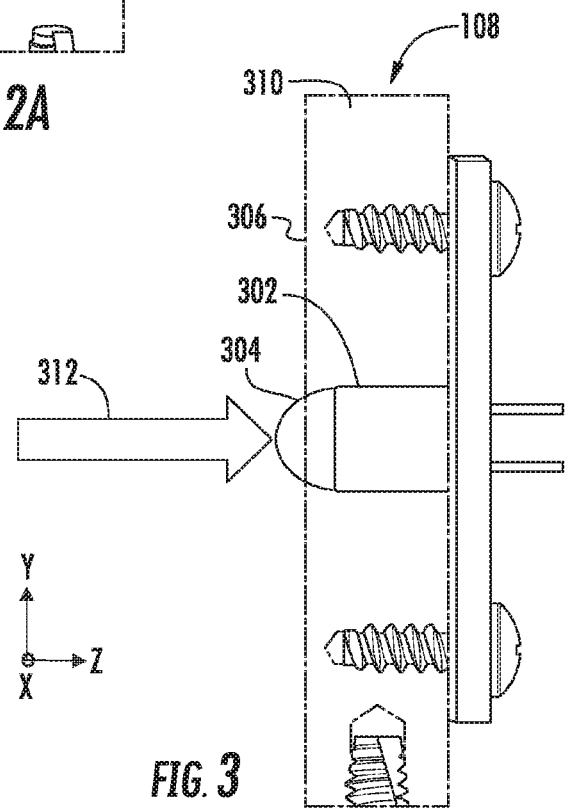
FIG. 3

SYSTEM AND METHOD FOR OZONE CONCENTRATION MEASUREMENT IN LIQUIDS HAVING A NEGATIVE SCALING INDEX

This is a national stage application filed under 35 U.S.C. § 371 of pending international application PCT/US2018/014768, filed Jan. 23, 2018, the entirety of which application is hereby incorporated by reference herein.

FIELD

The present embodiments relate to gas analyzer devices, more particularly, to gas concentration optical measurement apparatus for use in measuring ozone concentrations in liquids having a negative scaling index, or Langelier saturation index (LSI).

BACKGROUND

Gas concentration measurement devices are useful to detect various types of gases including ozone. One type of device takes advantage of the optical absorption of light that may pass through a sample of water or other liquid being measured. Ozone is known to strongly absorb light in the short wavelength ultra-violet region of the spectrum, sometimes referred to as UV-C radiation. By placing a source of UV-C radiation at a known distance from a UV-C radiation sensor the concentration of ozone may be determined by measuring the radiation loss and using known optical formula that calculate the absorption or loss of radiation between source and detector for a given concentration of ozone.

However, known systems may not be optimized to conveniently and rapidly measure low ozone concentrations. Additionally, measuring the ozone concentration over a wide range of concentrations using the same device may be useful. With respect to these and other considerations, the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In various embodiments, improved gas concentration measurement apparatus and techniques are provided. In one embodiment, an apparatus may include an emitter, the emitter comprising an ultraviolet light emitting diode (UV-LED) and being disposed on a first end of a bounded volume which is suitable for holding a liquid. The bounded volume can be a chamber, a tank, a piping section, or the like. The apparatus may also include a detector, the detector comprising an ultraviolet light sensor (UV sensor) and being disposed on a second end of the bounded volume, the second end being opposite the first end, wherein the UV-LED comprises a point source, and wherein the emitter generates a parallel beam of light.

In another embodiment, an apparatus may include a bounded volume which is suitable for holding a liquid; an emitter, the emitter comprising an ultraviolet light emitting diode (UV-LED) and being disposed on a first end of the bounded volume; a detector, the detector comprising an ultraviolet light sensor (UV sensor) and being disposed on a second end of the bounded volume, the second end being opposite the first end; an insert holder disposed in the bounded volume; and at least one optical insert, wherein the at least one insert is reversibly fixable to the insert holder, and wherein the at least one insert comprises a UV-transmitting material.

In a further embodiment, an apparatus may include a bounded volume which is suitable for holding a liquid. The apparatus may further include an emitter, where the emitter includes an ultraviolet light emitting diode (UV-LED) and being disposed on a first end of the bounded volume; and an emitter lens, the emitter lens coupled to the UV-LED, wherein the UV-LED is disposed at a first focus of the emitter lens. The apparatus may also include a detector, where the detector includes an ultraviolet light sensor (UV sensor) and being disposed on a second end of the bounded volume, the second end being opposite the first end; and a detector lens, the detector lens coupled to the UV sensor, wherein the UV sensor is disposed at a second focus of the detector lens. The apparatus may additionally include an insert holder disposed in the bounded volume; and at least one optical insert, wherein the at least one insert is reversibly fixable to the insert holder, and wherein the at least one insert comprises a UV-transmitting material.

BRIEF DESCRIPTION OF THE DRAWINGS

FIG. 2A depicts an emitter according to an embodiment of the disclosure;

FIG. 2B depicts details of the geometry of the emitter of FIG. 2A;

FIG. 3 depicts a detector according to an embodiment of the disclosure;

Figure 1A:
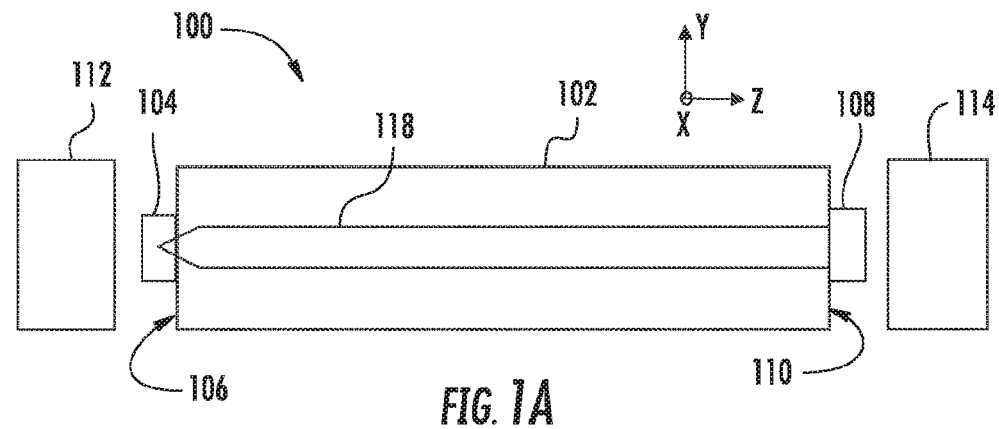
FIG. 1A depicts a side view of an apparatus according to various embodiments of the disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

The present embodiments will now be described more fully hereinafter with reference to the accompanying drawings, in which some embodiments are shown. The subject matter of the present disclosure, however, may be embodied in many different forms and should not be construed as limited to the embodiments set forth herein. Rather, these embodiments are provided so that this disclosure will be thorough and complete, and will fully convey the scope of the subject matter to those skilled in the art. In the drawings, like numbers refer to like elements throughout.

In various embodiments improved gas concentration measurement apparatus and techniques are presented. The present embodiments may be usefully employed for detection of gas concentrations for UV-absorbing gases, such as ozone. In particular, example non-limiting embodiments are related to optically transparent apparatus containing a liquid, which in some non-limiting example embodiments is referred to as a cuvette. A cuvette may be generally optically transparent and may enclose a contained liquid, such as water that is deliberately introduced into the cuvette. As detailed below, by employing an emitter to emit electromagnetic radiation into the cuvette into one end and detecting radiation transmitted out of the cuvette at another end, the gas concentration of a gas species within the liquid contained in the cuvette may be measured. In some embodiments, the liquid contained in the cuvette has a negative Langelier saturation index (LSI).

FIG. 1A depicts an apparatus 100 according to various embodiments of the disclosure. The apparatus 100 may include a bounded volume, such as a chamber 102, to house a liquid, which in one non-limiting example is water. In some embodiments, the water has a negative LSI. FIG. 1E depicts a perspective view of a variant of the apparatus of FIG. 1A, where the chamber 102 is shaped as a cylinder, although this is not critical and it will be appreciated that the chamber can assume other shapes. The chamber 102 may be arranged as a cuvette where the chamber 102 has a designed length along the Z-axis of the Cartesian coordinate system shown. The cuvette may have a rectangular cross-section (in the X-Y plane), square cross-section, circular cross-section, or other convenient shape in various non-limiting embodiments. In accordance with various embodiments, the cuvette length (or distance between radiation emitter and sensor) may be in the range of 0.25 centimeters (cm) to a few meters (m) depending on ozone concentration ranges.

As further shown in FIG. 1A, the apparatus 100 may include an emitter 104 disposed on a first end 106 of the chamber 102, and a detector 108 disposed on a second end 110 of the chamber 102. The emitter 104 may include an ultraviolet (UV) light emitting diode (UV-LED), where the UV-LED is designed to emit radiation having a wavelength arranged according to light absorption characteristics of a target gas or gases to be measured in the chamber 102. In other words, the wavelength or range of wavelengths of radiation emitted by the emitter 104 may be designed to overlap a wavelength or wavelength range where the target gas has a high degree of absorption. In this manner, the presence of a target gas may be detected by the attenuation of electromagnetic radiation directed into the chamber 102 when at least some photons of the radiation are absorbed by the gas.

In embodiments where the apparatus 100 is used as an ozone detector, the emitter 104 may include a UV-LED that emits radiation overlapping in wavelength with an optical absorption peak in ozone centered around 260 nanometers (nm) and having a half-width of approximately 20 nm (see also FIG. 4, discussed below). In particular embodiments, the emitter 104 may include a UV-LED that generates radiation in the range of 250 nanometers (nm) to 300 nm, and more particularly in the range of 250 nm to 270 nm. For example, a known UV LED may be designed to emit radiation over a narrow range, where greater than 75% of the electromagnetic radiation intensity is between 250 nm and 270 nm. This situation ensures that most photons emitted by the emitter 104 will have a wavelength overlapping a wavelength range of the absorption peak for ozone at 260 nm.

Turning now to the detector 108, in various embodiments the detector 108 may include a UV sensor 10, such as a solar blind UV photodiode. The term "solar blind" may refer to a detector that is not sensitive to solar radiation at the earth's surface, and in particular, may not be sensitive to radiation having wavelengths greater than 290 nm. As is known, the shortest wavelength of UV solar radiation generally incident at the earth's surface is UV-B radiation, whose range is between about 320 nm and 290 nm. Accordingly, the detector 108 may not be sensitive to background electromagnetic radiation (also referred to herein as "light") from the sun during normal operation. This insensitivity to background light facilitates more accurate detection of the concentration of a gas such as ozone, since the radiation being measured at detector 108 may be assumed to be generated from emitter 104.

A hallmark of the apparatus 100 is the configuration of the emitter 104. In particular, the emitter 104 may include various components as detailed below, where the emitter 104 acts as a point source of light. In this manner, radiation generated by the emitter 104 may be manipulated to generate a beam 118, composed as a parallel beam, meaning a beam composed of light having light rays that are parallel to one another. Moreover, the beam 118 may be conducted to the detector 108 along a trajectory lying parallel to the long axis of the chamber 102, that is, along the Z-axis. This geometry provides for more efficient generation and detection of the presence and concentration of a gas within a liquid disposed in the chamber 102 as compared to known ozone detectors. The apparatus 100 may further include a UV-LED power supply 112, arranged according to known power supplies to power the emitter 104, as well as an amplifier/microcontroller 114, coupled to the detector 108. Additionally, the apparatus 100 may include liquid conduits (not shown for clarity) to conduct liquid into and out of the chamber 102.

Figure 1B:
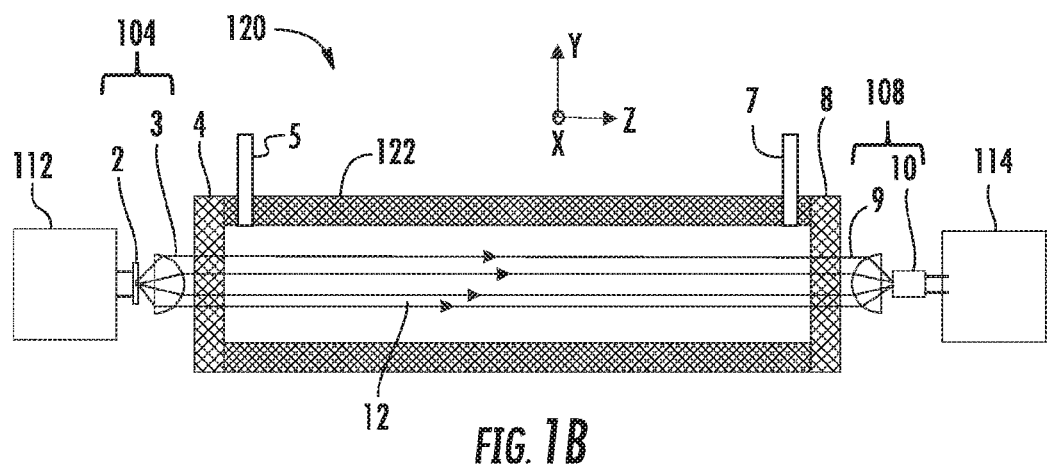
FIG. 1B depicts a side view of another apparatus according to various embodiments of the disclosure.

Turning now to FIG. 1B there is shown an apparatus 120 according to additional embodiments of the disclosure. In this embodiment, the emitter 104 is shown to include a UV-LED 2, whose operation may proceed as generally described above, as well as an emitter lens 3. In accordance with various embodiments of the disclosure, and as discussed in more detail below, the UV-LED 2 may be disposed at a focus of the emitter lens 3, which focus may be deemed a first focus. As suggested in FIG. 1B the emitter lens 3 may have a convex shape, and in some embodiments, may be a hemisphere. By situating the UV-LED 2 at a focus of the emitter lens 3, light emitted by the UV-LED 2 may have its rays collimated into a parallel beam of light, shown as beam 12. The emitter lens 3 may further be situated and oriented so as to generate the beam 12 in a manner where the trajectories of light rays of beam 12 lie parallel to the long axis (Z-axis) of the chamber 122.

As further shown in FIG. 1B, the apparatus 120 may include a first window, shown as window 4, where the window 4 is transparent to UV radiation, in particular, at wavelengths above 250 nm. A suitable UV-transmitting material for use as window 4, for example, is quartz, where transmission for a 10 millimeter (mm) thick material may exceed 90% at 250 nm wavelength of light. The embodiments are not limited in this context. Similarly, apparatus 120 may include a second window, shown as window 8, where the second window is transparent to UV radiation at least above 250 nm wavelength, and may be composed of the same material as window 4. The chamber 122 may, in non-limiting example embodiments, constitute a square cross-section tube, or a cylindrical tube that is capped at opposite ends using quartz windows (window 4 and window 8) and sealed by O-rings, on both ends.

In the embodiment of FIG. 1B, the detector 108 is shown as composed of a UV sensor 10, whose properties may be as described above, such as a solar-blind sensor. The detector 108 may further include a detector lens 9, where the detector lens 9 is disposed to intercept the beam 12, where the detector 108 is disposed at a second focus, that is, the focus of the detector lens 9. Notably, in other embodiments as in FIG. 1A, the detector 108 need not be disposed at the focus of a detector lens, and a detector lens need not be used at the detector 108. The use of a detector lens may enhance the amount of radiation detected, while the use of an emitter lens to generate a parallel beam may in some instances provide adequate radiation intensity to the detector 108 without need of a detector lens.

As further shown in FIG. 1B, the apparatus 120 may include a liquid inlet 5 to conduct liquid, such as water, into the chamber 102, and a liquid outlet 7 to conduct liquid out of the chamber 102. In operation of the apparatus 120, liquid (e.g., water) containing ozone or other gas species to be measured may be provided through liquid inlet 5, flowing through the chamber 102, and then out of chamber 102 through liquid outlet 7. The UV-LED 2 may then be energized, generating radiation that enters the chamber 102 via emitter lens 3 and first window 4 as a parallel UV beam, shown as beam 12. The beam 12 represents light whose direction of propagation is from left to right as shown by the arrows. As beam 12 traverses the chamber as a beam of parallel light having a predetermined wavelength, such as approximately 260 nm, some photons of beam 12 may be absorbed by a target gas (not shown) to be measured, such as ozone, due to the optical absorption characteristics of the target gas. By the time the beam 12 reaches the detector 108, the intensity of beam 12 may be reduced from a first intensity at the point of entering the chamber 102, to a second intensity at the point of exiting the chamber 102, where the second intensity is less than the first intensity. Since the beam 12 is beam of parallel light, by careful arrangement of the components of emitter 104 and components of detector 108, a large fraction of all the light emitted from emitter 104 that is not otherwise absorbed by gas in the chamber 102 may be collected by the detector 108. This facilitates better determination of the concentration of a given target gas species that may be present in a given overall liquid provided to the chamber 102, based upon the detected light intensity of beam 12 at detector 108.

In particular embodiments, the ozone concentration in a liquid provided to chamber 102 may be determined in the following manner. The intensity of UV radiation (I) of the beam 12 after absorption of part of radiation by ozone may be expressed as:

$$I = I_o * \exp(-K * C_{oz}) \qquad \text{Eq. (1),}$$

where I is UV intensity after absorption, Io is UV intensity without absorption (without any ozone), $C_{oz}$ is ozone concentration, and K is a coefficient depending on wavelength and units used, and proportional to cuvette length, that is, the length of chamber 102. In other embodiments, the term $C_{oz}$ may be replaced with the general term "C" to stand for the concentration of any gas being measured according to the absorption of UV radiation.

The ozone concentration in liquid present in the chamber 102 at a given instance may be calculated by the procedure described below. As an initial operation, a first automatic zeroing of readings of the apparatus 120 takes place. In the zeroing operation, the ozone concentration of the liquid in the chamber 102 should be arranged to be zero. For the zeroing operation, when zero ozone concentration is present in the chamber 102, a controller of an analog to digital device (see amplifier/microcontroller 114) takes digital readings (Uo) of a signal intensity from an amplifier that amplifies a signal from the UV sensor 10. On the basis of the value of Uo the parameter N may be calculated according to:

$$N = \text{Ln}(U\max/Uo) \qquad \text{Eq. (2),}$$

where Umax is maximal signal and Uo is the digital reading of a Digital-to-Analog converter (DAC) at the moment of zeroing. Merely as a non-limiting example, Umax may read 4.5 V, while Uo reads 3 V, without any ozone present in the liquid contained in the chamber 102. Then, intensity readings collected by apparatus 120 (which readings may be provided on a display) may be used to calculate C by:

$$C = (\text{Ln}(U\max/Uav) - N) * K \qquad \text{Eq. (3),}$$

where Uav is the average of actual digital readings of a DAC obtained during a given time. As a non-limiting example, a sampling interval for taking the digital readings in the presence of ozone may be from 1 second to 20 seconds. The embodiments are not limited in this context. The number of digital readings may vary, while in one implementation a reading may be taken every 0.1 seconds, meaning a sample size for calculating Uav may range up to 100 readings or more. The embodiments are not limited in this context. Following the above example where U0 is 3 V, the value of Uav may be 2.0 V, indicating the absorption of some of the radiation by the ozone. In some implementations, time of averaging may be installed in a program menu. K represents a calibrating coefficient (which may be installed in a program menu).

If ozone concentration is still zero and Uav is equal to Uo readings on the ozonometer will be equal to zero. In other cases where ozone is present in the liquid in the chamber 102, readings will be proportional to the ozone concentration in the liquid, and can be made equal to actual ozone concentration by changing of the coefficient K.

Because the intensity of UV light detected by the detector 108 is relatively high and stable, small differences in signal intensity may easily be discerned when ozone is present in the liquid in the chamber. In this manner, the apparatus 120 can measure small ozone concentrations with a fast response time, facilitating use of the apparatus 120 in automatic control systems, where ozone concentration may be measured and is some cases controlled in real time.

Figure 1C:
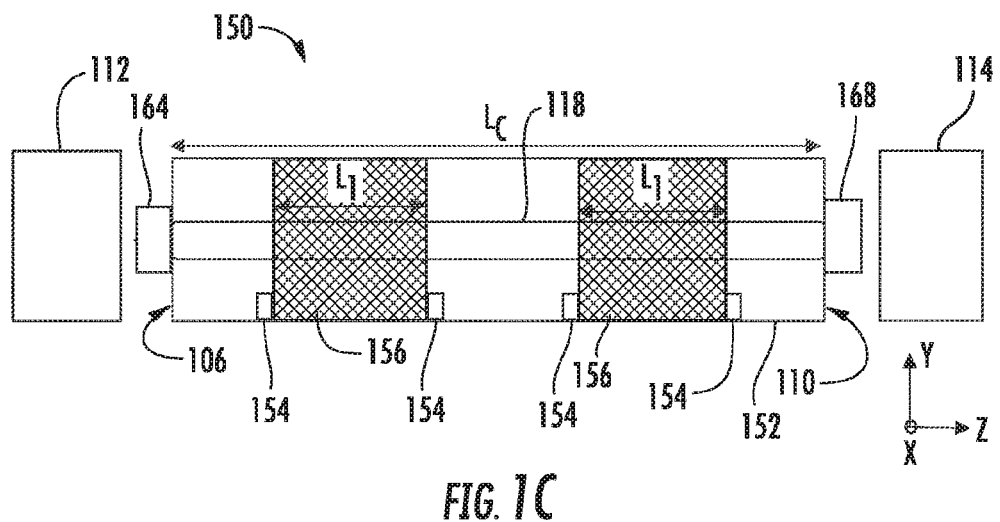
FIG. 1C depicts a side view of an additional apparatus according to various embodiments of the disclosure.

Turning now to FIG. 1C, there is shown another apparatus, apparatus 150, arranged according to further embodiments of the disclosure. The apparatus 150 may include similar components to those described above with respect to FIG. 1A and FIG. 1B. Liquid inlets and outlets are omitted for clarity. The apparatus 150 differs from apparatus 100 in that an insert holder 154 is disposed in the chamber 152. The insert holder 154 may be arranged wherein at least one insert, shown as inserts 156, is reversibly fixable to the insert holder 154. The inserts 156 may comprise a UV-transmitting material, such as quartz, so that just a small percentage of the beam 118 is absorbed by the inserts 156. Notably, the insert holder 154 is shown merely schematically, and may represent any known structure for holding an object, such as slots, recesses, tabs, clips, springs, and the like. Moreover, the holder 154 may represent any number of objects for holding any number of inserts.

When in place in the chamber 152, the inserts 156 reduce the path length of liquid through which the beam 118 travels between emitter 104 and detector 108. As shown, the length of the chamber 152, is shown as $L_C$ which is the distance between the inner surfaces of the windows 4 and 8. Absent inserts 156 in the chamber 152, the beam 118 travels through a path length where liquid is present equivalent to $L_C$ between emitter 104 and detector 108. When present, the inserts 156 reduce the path length of liquid through which the beam 118 travels between emitter 104 and detector 108 by an amount equal to the total length of the inserts 156 along the long axis of the chamber 152 (Z-axis), in this example, by an amount equal to $2(L_I)$, where $L_I$ is the length of an insert as shown. By appropriate choice of the total length of the inserts, the path length of the beam 118 may be reduced by 50%, 75%, 90%, or 99% with respect to an empty chamber, for example. The embodiments are not limited in this context. Notably, the illustration may not be drawn to scale. For example, in some embodiments the insert(s) 156 may occupy nearly all of the path length of liquid as compared to a chamber 152 without inserts. In particular examples, the total liquid path length, equivalent to $L_C-L_{Itot}$, where $L_{Itot}$ equals the total path through which beam 118 travels within the inserts 156 while traversing between the inner surfaces of windows 4 and 8, may equal as little 1 mm to 2 mm, and in some examples as little as 0.2 mm to 1 mm. This small path length of liquid may readily and accurately be provided by use of machined quartz inserts that are insertable into, for example, a cuvette having quartz windows at either end as described above. This reduction of path length renders the apparatus 150 especially useful for measuring high concentrations of a gas species, such as ozone, where the reduction of the signal of beam 118 by absorption from ozone may be unacceptably high when the beam 118 reaches detector 108 after traveling the distance $L_C$ through a liquid without the presence of inserts 156. On the other hand, the apparatus 150 provide a convenient configuration to also measure relatively lower concentrations of ozone, where the inserts 156 may be removed in the latter circumstance.

According to various embodiments, at the high ozone concentration range of measurement, concentrations of approximately 30 g/m³ to 300 g/m³ in the liquid may readily be measured using inserts 156. At the low ozone concentration range, with inserts 156 removed from chamber 152, concentrations below 30 g/m³ in the liquid may be measured.

Notably, the emitter 164 and detector 168 of apparatus 150 need not include the optics of the embodiments of FIG. 1A and FIG. 1B, where the emitter acts as a point source generating a parallel light beam between emitter 164 and detector 168. An advantage of providing removable inserts to reduce the path length of a beam through a liquid, is that the attenuation of light by a concentrated gas species may be maintained at an acceptable level, even if the light directed to the detector 168 is not a parallel beam of light.

Figure 1D:
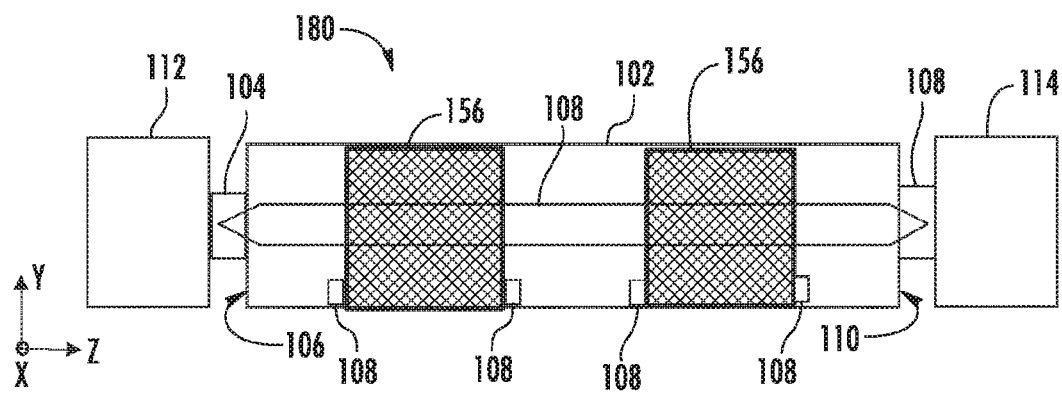
FIG. 1D depicts a side view of a further apparatus according to various embodiments of the disclosure.
Figure 1E:
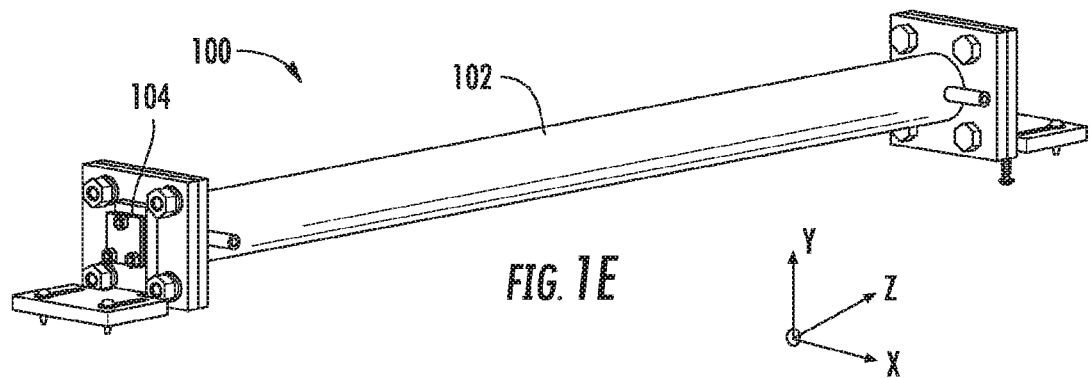
FIG. 1E depicts a perspective view of a variant of the apparatus of FIG. 1A.

Turning now to FIG. 1D there is shown an apparatus 180, arranged with the components as generally described above with respect to FIGS. 1A-1C. In this configuration, the emitter 104 and detector 108 may include the components as shown in FIG. 1B, providing a parallel beam of light between emitter 104 and detector 108, where a UV-LED is located at a focus of an emitter lens as described above. The apparatus 180 may be useful both for detection of small concentrations of ozone in the liquid as well as large concentrations of ozone in the liquid, where the inserts 156 are removable.

Figure 1F:
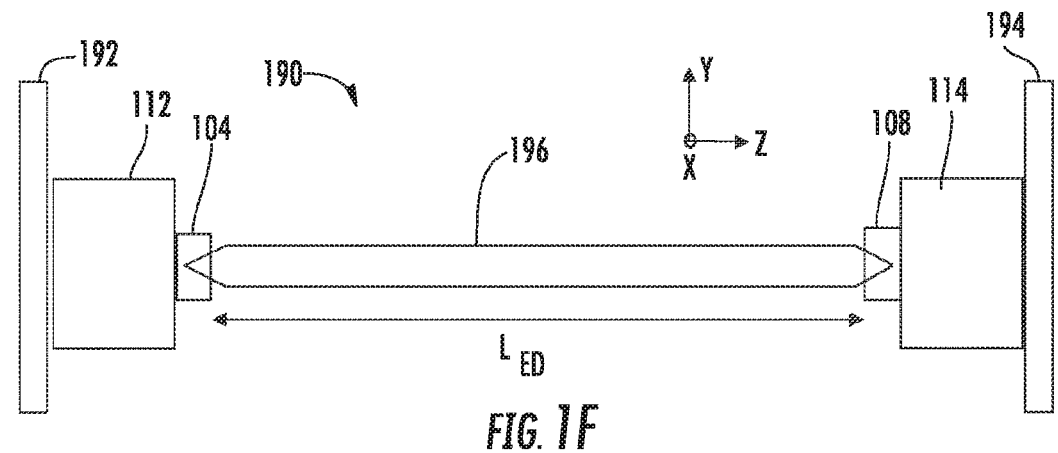
FIG. 1F depicts a side view of another apparatus according to various additional embodiments of the disclosure.

Turning now to FIG. 1F there is shown an implementation of an apparatus 190 according to further embodiments of the disclosure. In this example, the apparatus 190 may generally include the emitter components and detector components as detailed with respect to the above embodiments. A difference in this embodiment, is that the bounded volume may be in the form of a tank or other relatively large liquid-containing volume, rather than being a discrete chamber. Thus, with the illustrated embodiment the emitter 104 and detector 108 can be independently movable with respect to one another over relatively large distances (e.g., on the order of meters, depending on the size of the tank). For example, in FIG. 1F the emitter 104 may be arranged on a first wall 192 of a tank, while the detector 108 is arranged on a second wall 194 of the tank. The relative placement of the emitter 104 on wall 192 and placement of detector 108 on wall 194 and the optics of the emitter 104, including an emitter lens (not shown in FIG. 1F), may be aligned with the detector 108 so that the beam 196 is intercepted by the detector 108. This alignment may be aided by use of a laser or other convenient alignment device. Additionally, instead of a tank wall, the emitter 104, detector 108, or both, may be placed on other objects within, or otherwise associated with, a tank. In this manner, the ozone concentration or other gas concentration within an environment such as a tank may be conveniently measured. In some examples, because the emitter 108 provides a parallel beam of light, in the apparatus 190 the distance between emitter 104 and detector 108 may range up to 30 meters, providing a convenient method for measuring low concentrations of a gas within a large tank that may be used to store or transfer a relatively large liquid volume. The apparatus 190 provides the additional advantage of flexibility in the placement of an ozone or other gas detector within many different environments, in that the emitter 104 and detector 108 are not tethered to one another and may operate over a wide range of distances.

FIG. 2A depicts a variant of the emitter 104, according to an embodiment of the disclosure, while FIG. 2B depicts details of the geometry of the emitter of FIG. 2A. As shown, the emitter 104 may include a UV-LED 202, an emitter lens 204, an adjustment component 206, a substrate 208, spacer 210. Also shown in FIG. 2A is a window 212, where the window 212 may be a quartz window mountable on an end of a chamber, as described with respect to FIG. 1B, for example. As noted above, the UV-LED 202 may be designed to emit radiation of a target wavelength, such as the wavelength range of the absorption peak of ozone at approximately 260 nm. The UV-LED 202 may be surface mounted on a printed circuit board, as represented by the substrate 208.

As shown in FIG. 2A, the adjustment component 206 may be a set of bolts and nuts, or other fastening device that engages the substrate 208 and window 212. The spacer 210 may represent a set of spacers such as washers, where at least one washer may be inserted on a given bolt between the substrate 208 and window 212. As further shown in FIG. 2A, the emitter lens 204 may have a generally hemispherical shape and may be affixed within a cavity provided in the window 212. Because the emitter lens 204 is affixed to the window 212, while the UV-LED 202 is affixed to the substrate 202, the distance between the emitter lens 204 and UV-LED 202 may be adjusted by adjusting the spacing between substrate 208 and window 212. This adjustment of spacing may be accomplished by the choice of the thickness of spacer 210, as well as the number of spacers 210 to be arranged on a given adjustment component, such as a bolt. Turning now to FIG. 2B, there is shown the geometry of light emitted by UV-LED 202. The rays 216 that are emitted from the UV-LED 202 may form a cone that is received by the emitter lens 204. By proper adjustment of the spacing S along the Z-axis between the emitter lens 204 and UV-LED 202, the UV-LED 202 may be maintained just at the focus 216 of the emitter lens 204, ensuring that light emerging to the right from the emitter lens 204 forms a parallel beam 220.

FIG. 3 depicts a variant of the detector 108 according to an embodiment of the disclosure. In this example, the detector includes an optical sensor 302, which sensor may be mounted in a window 310, such as a quartz window mounted on an end of a chamber. The detector 108 may include a detector lens 304, where the detector lens 304 is arranged to collect a beam 312 of parallel light and to focus the beam 312, where the focus of the detector lens 304 may coincide with the position of a sensing element (not separately shown) of the optical sensor 302.

Figure 4:
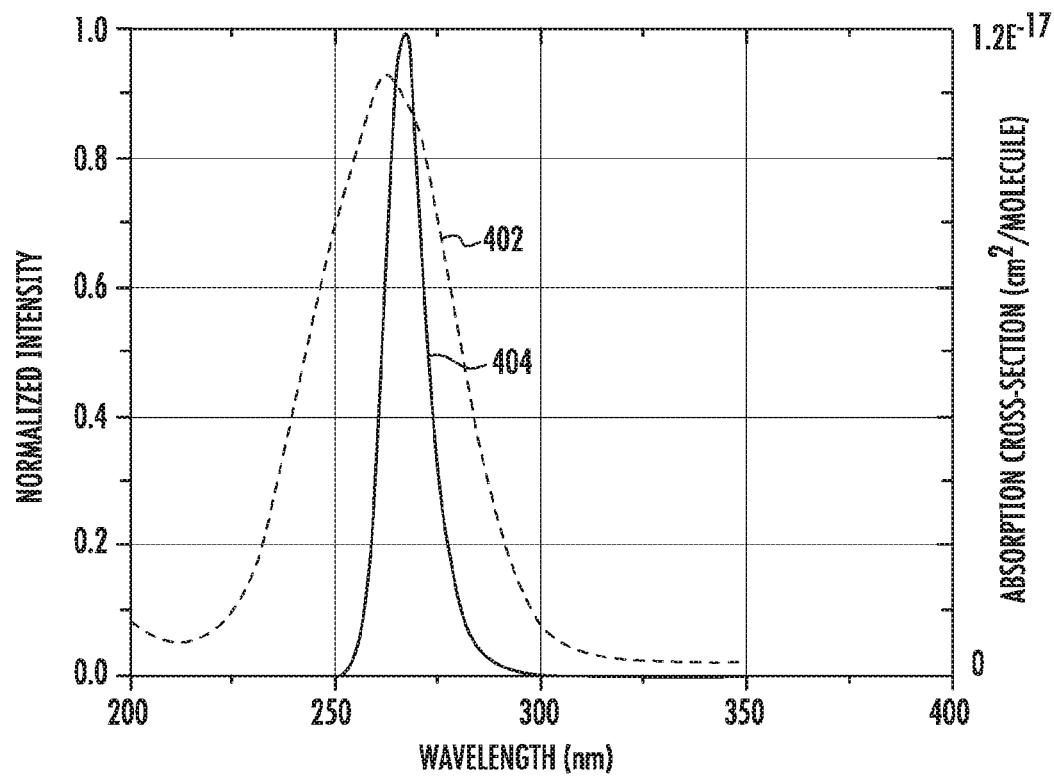
FIG. 4 is a composite graph depicting optical properties of ozone and an emitter, according to an embodiment of the disclosure.

To further illustrate the operating principles of an apparatus according to the present embodiments, FIG. 4 is a composite graph depicting optical properties of ozone and an emitter, according to an embodiment of the disclosure. In FIG. 4 a curve 402 illustrates an absorption peak for ozone, showing that the cross-section for absorption has a maximum at approximately 260 nm, while no absorption of light takes place above approximately 325 nm. Also shown is an emission spectrum of an exemplary UV-LED, shown as curve 404. The curve 404 is sharply peaked at approximately 265 nm, showing that nearly 100% of radiation of curve 404 overlaps with a wavelength range where the absorption of light by ozone molecules is high.

Figure 5:
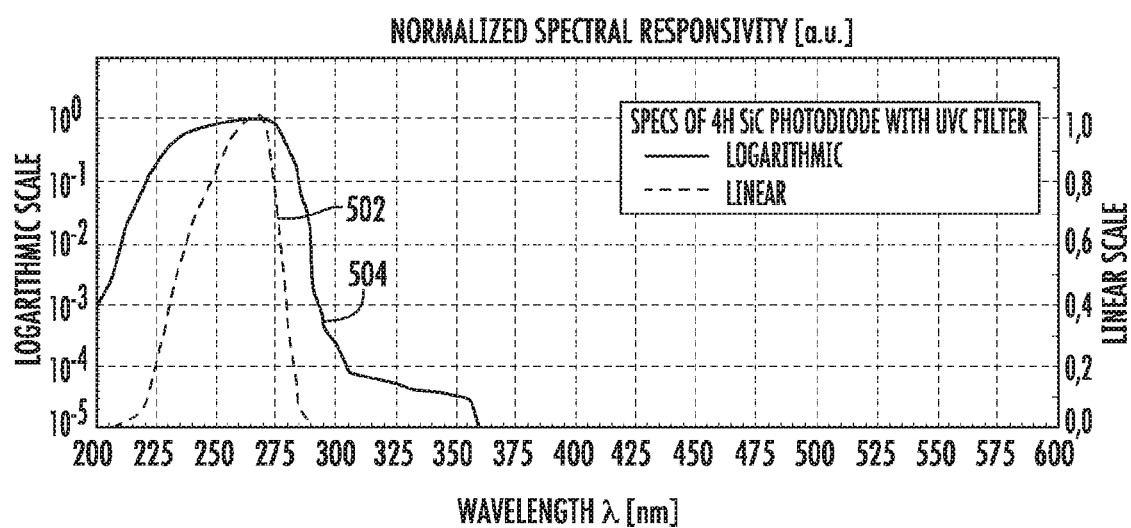
FIG. 5 is graph depicting optical properties of a detector according to an embodiment of the disclosure.

To further illustrate principles of detection, FIG. 5 is graph depicting optical properties of a detector according to an embodiment of the disclosure. In FIG. 5, the same data of silicon carbide photodiode with a radiation filter is shown as two different curves, linear curve 502, and logarithmic curve 504. As shown, a peak in responsivity takes place at 270 nm, while little radiation is detected above 290 nm wavelength. Accordingly, the detector device providing the data of FIG. 5 is suitable to detect radiation generated by the emitter device providing the data of curve 404.

FIGS. 6-9 depict various specific arrangements of emitters and detectors for determining the concentration of dissolved ozone in a liquid disposed in a tank or other container, similar to the arrangement described in relation to FIG. 1F. It will be appreciated that for the arrangements disclosed in FIGS. 6-9, dissolved ozone concentration can be calculated or otherwise determined in the manner(s) disclosed in relation to the previous embodiments.

Figure 6:
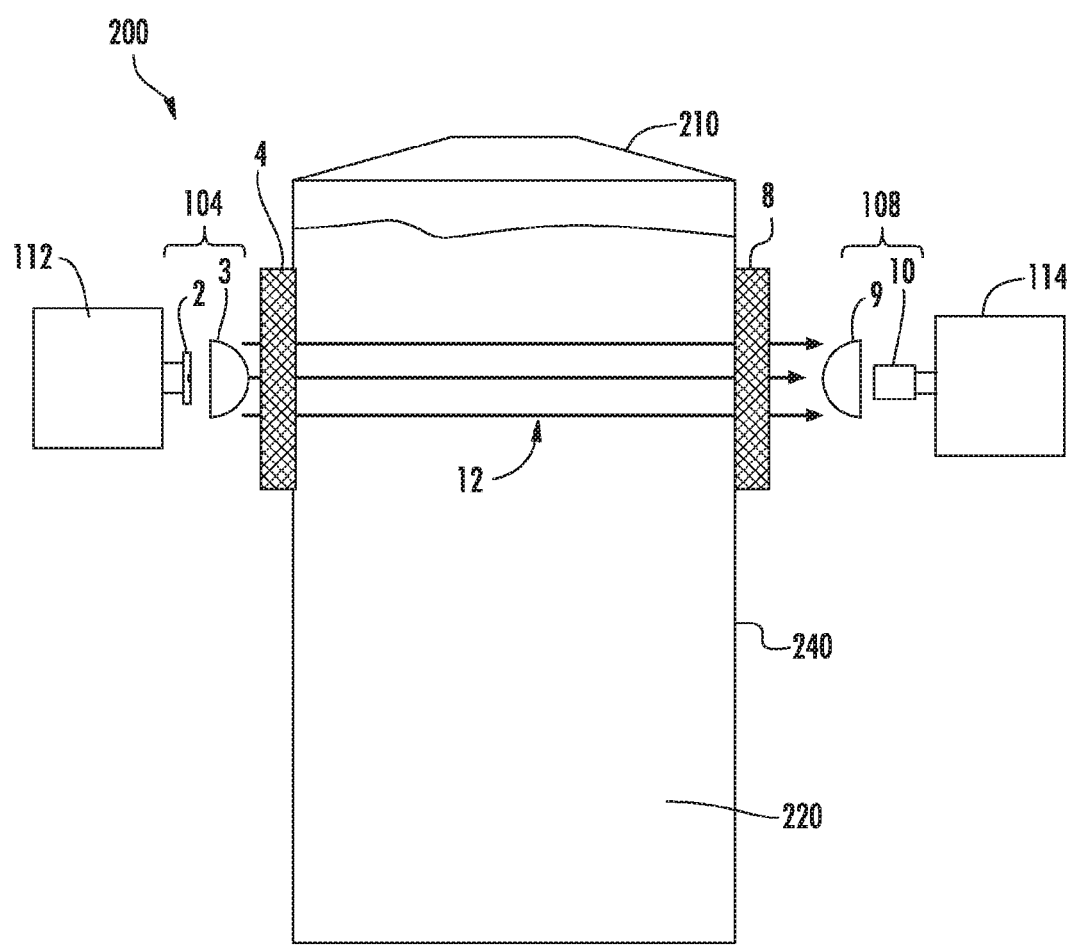
FIGS. 6-9 depict various arrangements of an emitter and detector positioned in various relationships with respect to a tank containing a liquid.

FIG. 6 illustrates an embodiment of the disclosed apparatus 200 in which the emitter 104 of UV radiation and the UV detector 108 are installed outside of a tank 210 containing a liquid 220 in in which a concentration of dissolved ozone is to be measured. In non-limiting example embodiments, the liquid 220 is water having a negative LSI. As will be understood, the illustrated apparatus 200 can include emitter components (e.g., UV LED 2, emitter lens 3) and detector components (e.g., detector lens 9, UV sensor 10) as detailed with respect to the previous embodiments. In the present embodiment, first and second sealed quartz windows 4, 8 are installed in or on opposing first and second walls 230, 240 of the tank 210. The emitter 104 may be positioned adjacent the first wall 230 and first window 4, while the detector 108 may be positioned adjacent the second wall 240 and second window 8. The relative placement of the emitter 104 on wall 230 and placement of detector 108 on wall 240, as well as the optics of the emitter 104 (including emitter lens 3), may be as appropriate to align with the detector 108 so that the beam 12 is intercepted by the detector 108. This alignment may be aided by use of a laser or other convenient alignment device.

Figure 7:
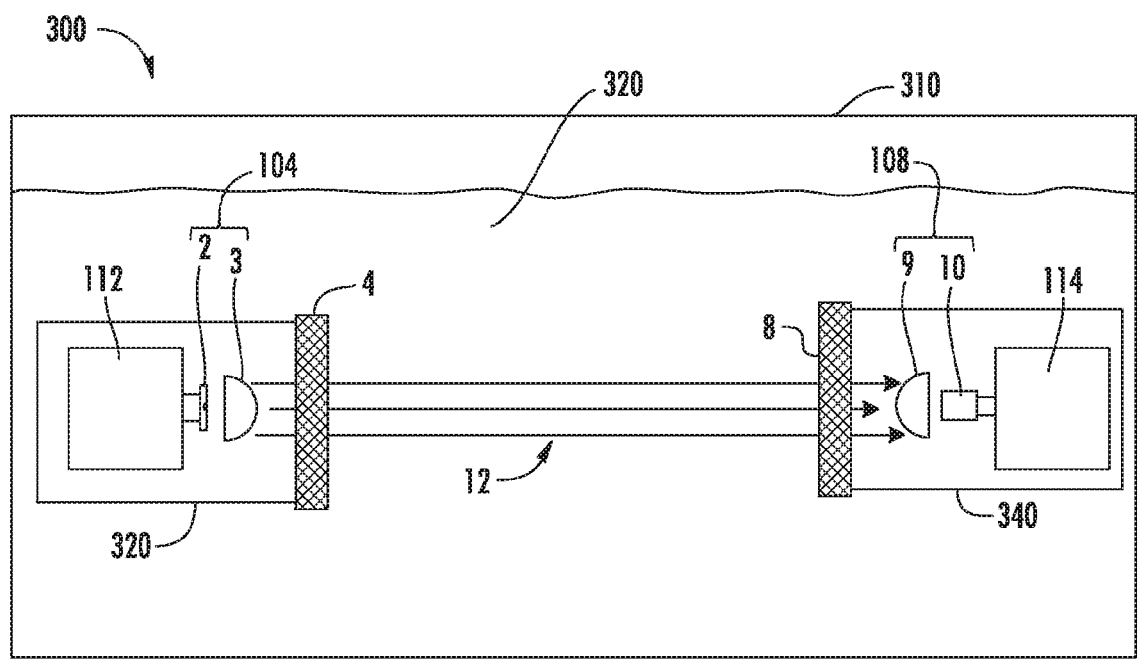

FIG. 7 illustrates an embodiment of the disclosed apparatus 300 in which the emitter 104 of UV radiation and the UV detector 108 are installed within a tank 310 containing a liquid 320 in in which a concentration of dissolved ozone is to be measured. In non-limiting example embodiments, the liquid 320 is water having a negative LSI. As will be understood, the illustrated apparatus 300 can include emitter components (e.g., UV LED 2, emitter lens 3) and detector components (e.g., detector lens 9, UV sensor 10) as detailed with respect to the previous embodiments. In the present embodiment, the emitter 104 and detector 108 are disposed within first and second sealed enclosures 330, 340 respectively, to prevent ingress of liquid from the tank. First and second sealed quartz windows 4, 8 can be installed in or on the sealed enclosures 330, 340, and the components may be positioned so that the beam 12 from the emitter 104 is directed through the first window 4, through the liquid 320, through the second window where it is intercepted by the detector 108. As with previous embodiments, alignment may be aided by use of a laser or other convenient alignment device.

Figure 8:
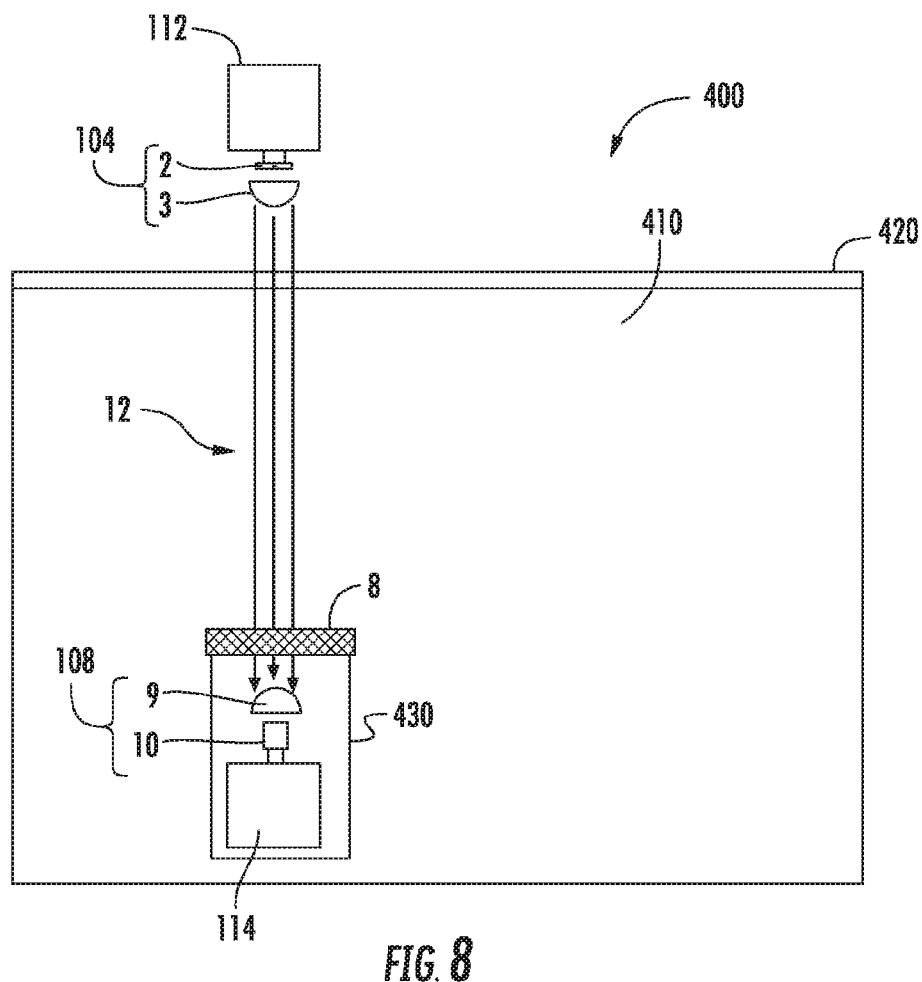

FIG. 8 illustrates an embodiment of an apparatus 400 for use in measuring a concentration of dissolved ozone in a liquid 410 disposed in a tank 420. In this embodiment, the emitter 104 of UV radiation is positioned outside of the tank 420 while the UV detector 108 is positioned within the tank. In non-limiting example embodiments, the liquid 410 is water having a negative LSI. As will be understood, the illustrated apparatus 400 can include emitter components (e.g., UV LED 2, emitter lens 3) and detector components (e.g., detector lens 9, UV sensor 10) as detailed with respect to the previous embodiments. In this embodiment, the detector 108 are disposed within a sealed enclosure 430 to prevent ingress of liquid from the tank. A sealed quartz window 8 is installed in or on the sealed enclosure 430, and the components may be positioned so that the beam 12 from the emitter 104 is directed through the liquid 410, through the window 8 where it is intercepted by the detector 108. As with previous embodiments, alignment may be aided by use of a laser or other convenient alignment device.

Figure 9:
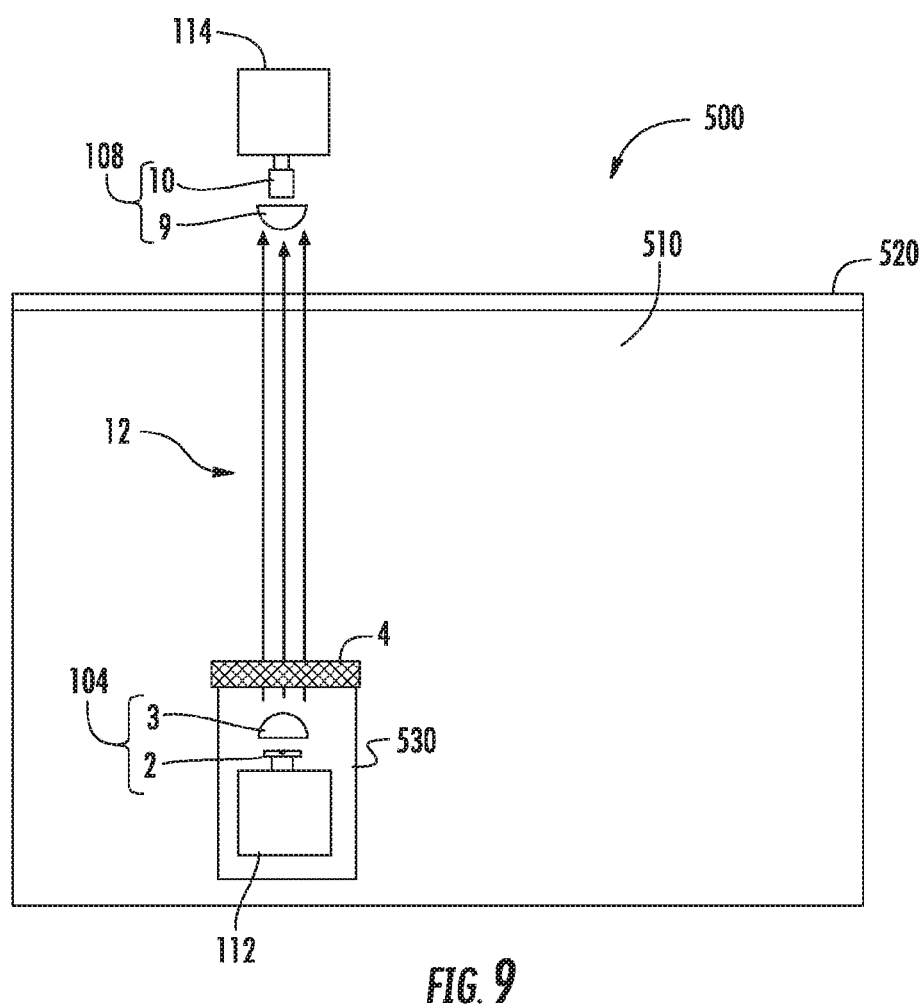

FIG. 9 illustrates an embodiment of an apparatus 500 for use in measuring a concentration of dissolved ozone in a liquid 510 disposed in a tank 520. In this embodiment, the emitter 104 of UV radiation is positioned inside of the tank 520 while the UV detector 108 is positioned outside the tank. In non-limiting example embodiments, the liquid 510 is water having a negative LSI. As will be appreciated, the illustrated apparatus 500 can include emitter components (e.g., UV LED 2, emitter lens 3) and detector components (e.g., detector lens 9, UV sensor 10) as detailed with respect to the previous embodiments. In this embodiment, the emitter 104 is disposed within a sealed enclosure 530 to prevent ingress of liquid from the tank. A sealed quartz window 4 is installed in or on the sealed enclosure 530. The components may be positioned so that the beam 12 from the emitter 104 is directed through the window 4, through the liquid 510 and is intercepted by the detector 108 outside the tank 520. As with previous embodiments, alignment may be aided by use of a laser or other convenient alignment device.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are in the tended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Thus, the claims set forth below should be construed in view of the full breadth and spirit of the present disclosure as described herein.

What is claimed is:

1. An apparatus, comprising:
   an emitter comprising an ultraviolet light emitting diode (UV-LED) and a convex lens such that the UV-LED is at a focus of the convex lens, the emitter being positionable on a first end of a bounded volume, the bounded volume comprising a chamber configured to contain a liquid having a negative LSI; and
   a detector comprising an ultraviolet light sensor (UV sensor) and being positionable on a second end of the bounded volume, the second end being opposite the first end, wherein the UV-LED comprises a point source, and wherein the emitter generates a parallel beam of light;
   wherein the detector is configured to collect light emitted by the emitter that has not been absorbed by a gas dissolved in the liquid;
   wherein the bounded volume comprises:
     a first window disposed on the first end of the chamber; and
     a second window disposed on the second end of the chamber, the first window and the second window comprising a UV-transmitting material;
   wherein the apparatus further comprises:
     an insert holder is disposed in the chamber; and
     at least one optical insert, wherein the at least one insert is reversibly fixable to the insert holder, and wherein the at least one insert comprises a UV-transmitting material.

2. The apparatus of claim 1, wherein the UV-LED comprises an emitter generating radiation in the range of 250 nm to 270 nm.

3. The apparatus of claim 1, wherein the UV sensor comprises a solar blind UV photodiode.

4. The apparatus of claim 1, wherein the emitter comprises an emitter lens, the emitter lens movably coupled to the UV-LED, wherein a position of the UV-LED is adjustable so as to be disposed at a first focus of the emitter lens.

5. The apparatus of claim 4, wherein the convex lens comprises a hemisphere.

6. The apparatus of claim 1, wherein the detector comprises a detector lens, the detector lens coupled to the UV sensor, wherein the UV sensor is disposed at a second focus of the detector lens.

7. The apparatus of claim 6, wherein the detector lens comprises a convex lens.

8. The apparatus of claim 1, further comprising:
   a liquid inlet to conduct the liquid into the chamber, and
   a liquid outlet to conduct the liquid out of the chamber.

9. The apparatus of claim 1, wherein the emitter and the detector are independently movable with respect to one another.

10. The apparatus of claim 9, wherein the emitter and detector are independently movable with respect to each other so as to align the emitter and detector such that the UV-LED emits the light that can be captured by the detector.

11. An apparatus, comprising:
    a bounded volume for housing a liquid having a negative LSI;
    an emitter, the emitter comprising an ultraviolet light emitting diode (UV-LED) and being disposed on a first end of the bounded volume;
    a detector, the detector comprising an ultraviolet light sensor (UV sensor) and being disposed on a second end of the bounded volume, the second end being opposite the first end;
    an insert holder disposed in the bounded volume; and
    at least one optical insert, wherein the at least one insert is reversibly fixable to the insert holder, and wherein the at least one insert comprises a UV-transmitting material.

12. The apparatus of claim 11, wherein the UV-LED comprises an emitter generating radiation in the range of 250 nm to 270 nm.

13. The apparatus of claim 11, wherein the UV sensor comprises a solar blind UV photodiode.

14. The apparatus of claim 11, wherein the emitter comprises an emitter lens, the emitter lens movably coupled to the UV-LED, wherein a position of the UV-LED is adjustable so as to be disposed at a first focus of the emitter lens.

15. The apparatus of claim 11, wherein the detector comprises a detector lens, the detector lens coupled to the UV sensor, wherein the UV sensor is disposed at a second focus of the detector lens.

16. The apparatus of claim 11, wherein the bounded volume comprises a chamber, the apparatus further comprising:
    a first window disposed on the first end of the chamber; and
    a second window disposed on the second end of the chamber, the first window and
    the second window comprising a UV-transmitting material.

17. The apparatus of claim 11, wherein the bounded volume comprises a path length of liquid traversed by a beam emitted by the UV-LED between the emitter and the detector, wherein the path length of liquid is between 0.2 mm and 1 mm when the at least one insert is affixed to the insert holder.

18. An apparatus, comprising:
    a bounded volume for housing a liquid having a negative LSI;
    an emitter, the emitter comprising:
      an ultraviolet light emitting diode (UV-LED) and being disposed on a first end of the bounded volume; and an emitter lens, the emitter lens coupled to the UV-LED, wherein the UV-LED is disposed at a first focus of the emitter lens;
a detector, the detector comprising:
   an ultraviolet light sensor (UV sensor) and being disposed on a second end of the bounded volume, the second end being opposite the first end; and
   a detector lens, the detector lens coupled to the UV sensor, wherein the UV sensor is disposed at a second focus of the detector lens;
an insert holder disposed in the bounded volume; and
at least one optical insert, wherein the at least one insert is reversibly fixable to the insert holder, and wherein the at least one insert comprises a UV-transmitting material.

* * * * *